United States Patent [19]

Tomomatsu

[11] 3,935,252

[45] Jan. 27, 1976

[54] METHOD OF MANUFACTURING FUNGIBLE POLYTETRAMETHYLENE ETHER GLYCOL

[75] Inventor: Hideo Tomomatsu, Crystal Lake, Ill.

[73] Assignee: The Quaker Oats Company, Chicago, Ill.

[22] Filed: Sept. 18, 1974

[21] Appl. No.: 566,968

[52] U.S. Cl................. 260/346.1 R; 260/615 P
[51] Int. Cl.²............................................ C07D 307/34
[58] Field of Search ........ 260/346.1, 616, 615, 708, 260/601 R; 210/24

[56] References Cited
UNITED STATES PATENTS 2,818,449  12/1957  Christensen et al. ................ 210/24

OTHER PUBLICATIONS

Aripov et al., Chem. Abstracts, Vol. 77, Item 52681 (1972).

*Primary Examiner*—Harry I. Moatz
*Attorney, Agent, or Firm*—Joseph P. O'Halloran

[57] ABSTRACT

Disclosed herein is a method which provides substantially zero acid number polytetramethylene ether glycol thus making it possible to regard polytetramethylene ether glycol as a fungible commodity. The improvement is achieved by complete removal of a trace impurity, believed to be n-butyl aldehyde, from dry tetrahydrofuran, by contact with molecular sieves of a particular definition, prior to the polymerization of the tetrahydrofuran in the production of polytetramethylene ether glycol.

3 Claims, No Drawings

METHOD OF MANUFACTURING FUNGIBLE POLYTETRAMETHYLENE ETHER GLYCOL

BACKGROUND OF THE INVENTION

Tetrahydrofuran is polymerized to manufacture polytetramethylene ether glycol, which is also referred to as poly(tetramethylene glycol) in the patent art. However, depending on source polytetramethylene ether glycol which is presently commercially available has low but significant levels of acidity which are practically irreducible from a commercial viewpoint. Acidity in the polytetramethylene ether glycol disturbs the stoichiometry of the isocyanate ingredient when the polytetramethylene ether glycol is used in the manufacture of polyurethane polymers, and strict stoichiometry is essential in the preparation of many thermo plastic polyurethane polymers. In addition, the presence of acidity may accelerate the rate of the isocyanate reaction leading to inconsistent and inconstant operating results when the polytetramethylene ether glycol varies from time to time in acid number. Also it is well appreciated that the presence of substantial acidity in the polytetramethylene ether glycol adversely affects some catalyst systems, also resulting in inconstant and inconsistent operations from day to day with respect to the manufacture of polyurethane polymers therefrom.

Thus, because of the relatively low levels of acidity, and because of the profound impact of acidity with respect to the operational characteristics of polytetramethylene ether glycol, commercially available polytetramethylene ether glycol has not been regarded as fungible goods. Thus, a large scale user of polytetramethylene ether glycol in the manufacture of polyurethane polymers is confronted with varying acid levels if multiple sources of the polymeg are to be relied on and this would result in erratic and inconsistent and inconstant operations and products. On the other hand, once a manufacturer of polyurethane polymers has polytetramethylene ether glycol of a particular acid number level in his storage facility it is understandable that he is reluctant to intermingle with this material polytetramethylene ether glycol of the same molecular weight from a different source and having a different acid number. This has resulted in a tendency on the part of purchasers of polytetramethylene ether glycol to cut out a source of polytetramethylene ether glycol other than the original source thus substantially reducing competition.

Polytetramethylene ether glycol is manufactured by the polymerization of tetrahydrofuran, U.S. Pat. No. 3,454,652 to Andrew P. Dunlop and Edward Sherman lists a large number of tetrahydrofuran polymerization catalysts. Tetrahydrofuran is polymerized by the admixing of a tetrahydrofuran polymerization catalyst with tetrahydrofuran and the resulting admixture is the so-called "living polymer" or catalytically active polymerization mixture. In accordance with the procedure of the aforementioned patent the equilibrium is shifted in favor of the polymer by lowering the temperature, but in any event the catalytic activity of the catalytically active tetrahydrofuran-catalyst mixture is terminated in due course by the addition of a catalytic activity terminating agent such as, for example, water or 1,4-butane diol. The resulting catalytically inactive admixture is then typically worked up by steaming, for example, or water washing, decanting to remove water, and treatment with organic solvents to further remove water. Typically the acidic residue remaining from the catalyst are neutralized by the addition of excess quantities of a solid calcium hydroxide, and in addition other solid adsorbents may be used to assist in the further purification of the polytetramethylene ether glycol. Thereafter the polytetramethylene ether glycol is filtered and subjected to vacuum distillation to remove organic solvents and traces of water. Nonetheless it has been found that regardless of the extent to which the polytetramethylene ether glycol is water-washed, or to which it is subjected to the solid alkaline neutralizing agents there appears to be a level of acidity which is reached and which has been apparently irreducible from a commercial point of view. These apparently irreducible levels may be quite low, for example, 0.01 to 0.05 mg. KOH/gram acid number, but nonetheless variations in this acid number causes the goods to be regarded as non-fungible commodities. Various systems and schemes have been suggested for reducing the acid number of the polytetramethylene ether glycol but it must be appreciated that mere reduction of the acid number to any level other than zero does not place the polytetramethylene ether glycol in the category of a fungible commodity because of the profound impact of acid number on the operating characteristics of the polytetramethylene ether glycol in polyurethane polymerizations.

It is an object of the present invention to provide a method of manufacturing polytetramethylene ether glycol in which the level of acidity is substantially zero thus providing the art, for the first time, with a means of placing polytetramethylene ether glycol in the category of fungible goods.

THE INVENTION

Recent investigations have indicated a correlation between the presence of an impurity in low levels in tetrahydrofuran with the presence of the apparently irreducible acid level in the polytetramethylene ether glycol made therefrom. While it is not our intention to be bound by any theories it appears that the low level impurities in the tetrahydrofuran which correlates with the acid number in the polytetramethylene ether glycol is n-butyl aldehyde. Although a number of systems were found to reduce the level of n-butyl aldehyde it would found that merely reducing the n-butyl aldehyde level by absorption, for example, would not result in the reduction of the impurity to substantially zero, and would not result in the apparently irreducible level of acidity in the polytetramethylene ether glycol made therefrom to zero.

I have discovered that the irreducible acid level of polytetramethylene ether glycol made by the polymerization of tetrahydrofuran can be reduced to zero by first contacting the dry tetrahydrofuran with a molecular sieve having an average pore size in the range of 4–5 A, which molecular sieve adsorbent which is further characterized as having heat of adsorption of about 1,800 btu/pound of water ± 100 btu/pound of water.

Molecular sieves are described as the crystalline zeolites having a basic formula of $M_{2/n}O.Al_2O_3.XSiO_2.YH_2O$ where M is a cation of N valence and the values for X and Y fall into a definite range for a particular crystalline zeolite. The molecular sieves have been widely used and are well known in commerce.

Molecular sieves are described as crystalline metal alumino silicates with a three dimensional interconnecting network structure. The characterization, preparation, activation, and regeneration of molecular sieves is well described in the public literature. See, for example, U.S. Pat. Nos. 2,882,243 and 2,882,244 to Robert C. Milton. Molecular sieves which otherwise meet the requirements set forth herein, in accordance with this invention, can be prepared, activated, and regenerated, in accordance with the procedures outlined in the aforementioned patents, which patents are incorporated herein by reference thereto. The basic structure of the alumino silicates for use in the present invention are represented by the sodium form in which some or all of the sodium may be replaced by calcium, for example, to provide effective pore sizes of about 4 to 5 A. It will be appreciated by those skilled in the molecular sieve art that two terms are commonly used in connection with the description of the pores in the molecular sieves. It is generally believed that the elasticity, flexibility, and kinetic energy of incoming molecules allows passage of molecules up to about 0.5 A larger than the free diameter of the aperture. Consequently, in describing the molecular sieves, distinction must be made between the actual diameters of the structural aperture of the molecular sieve, and the effective molecular diameters of molecules which pass through these apertures. Generally speaking, in accordance with the present invention, molecular sieves having structural apertures in the range from about 3.5 to 4.5 A are useful. Since slightly larger diameter molecules can pass through apertures of this size, the sieves can be considered as having an effective pore size which is equal to the diameter of molecules which can pass therethrough. Hence, such molecular sieves are alternatively described as having effective pore sizes or nominal pore sizes in the range from about 4 to 5 A inclusive. In addition, the molecular sieves which are found to be useful herein have also been described in present U.S. commercial literature as molecular sieves of type A, and in particularly as types 4A and 5A.

It will be appreciated from consideration of the illustrative examples herein that the particular pore size is critical in accordance with the present invention but moreover the chemical characteristics of the sodium or calcium alumino silicate must be such that the heat of water adsorption is approximately 1800 btu/pound $H_2O$. Utilization of molecular sieves having effective pore sizes in the 4–5 A range but having thermodynamic properties such that the heat of water adsorption is lower e.g. less than 1,500 btu/pound $H_1O$, is not in accordance with the present invention, and did not result in the reduction of the irreducible acid number in the polytetramethylene ether glycol to 0.000 mg/KOH/gram.

Also, in accordance with the present invention, the tetrahydrofuran which is contacted with the molecular sieve is substantially anhydrous, that is, has a water content of less than about 0.5 percent preferably less than 0.1 percent w/w prior to passage through the molecular sieve bed. In a preferred embodiment the tetrahydrofuran is passed in the liquid phase over a stationary bed of the molecular sieve as defined herein.

Polytetramethylene ether glycol made from tetrahydrofuran which has been treated in this way give an acid number of 0.000 mg. KOH/gram when subjected to the same standard procedures which otherwise result in erratic but substantial positive acidity levels.

The invention will be further illustrated with the aid of the examples herein which are provided for illustrative purposes only and are not intended to unduly limit the scope of the invention nor to unduly limit the scope of the claims appended hereto. As used herein, and unless otherwise specifically stated, all parts are in parts by weight, all temperatures are in degrees centigrade, and acid numbers are expressed as mg.KOH/gram of material.

In the following examples the treatment of the tetrahydrofuran with molecular sives, in accordance with the present invention, is first described. The utilization of the tetrahydofuran thus purified in accordance with the present invention in the manufacture of polytetramethylene ether glycol is then illustrated. It will be apparent from the following illustrative examples that treatment of the tetrahydrofuran in accordance with the present invention reduces the percent butyl aldehyde to substantially zero, and it will also be apparent that, when the butyl aldehyde-free tetrahydrofuran was used in the manufacture of polytetramethylene ether glycol the irreducible acid level of the polytetramethylene ether glycol was reduced to 0.000.

EXAMPLE 1

350 parts of dry, liquid tetrahydrofuran containing 400 ppm of n-butyl aldehyde was passed through a 1 inch diameter by 6 inch depth bed of solid molecular sieve having an empirical chemical formula of $Na_{12}\cdot[(AlO_2)_{12}(SiO_2)_{12}]\cdot XH_2O$, having an effective pore size of 4 A and heat of adsorption of slightly under 1,800 btu/pound $H_2O$. The molecular sieve bed and the tetrahydrofuran which was treated by passage through the bed were at room temperature during the contacting. The tetrahydrofuran being charged to the bed had a water content of approximately 0.05 percent.

The tetrahydrofuran so purified was found to contain no detectable butyl aldehyde by gas chromatography analysis.

EXAMPLE 2

The purpose of this example is to illustrate the use of various molecular sieves for the purpose of treating tetrahydrofuran for the removal of n-butyl aldehyde, and to illustrate that generally speaking molecular sieves are ineffective in the reduction of the butyl aldehyde level to substantially zero, even in the 1,700–1,800 btu/pound $H_2O$ heat of adsorption.

The procedure of Example 1 was repeated except that a number of different respective samples of tetrahydrofuran containing approximately 0.05 percent water and varying amounts of butyl aldehyde were passed through respective molecular sieve beds. In this example a number of different respective molecular sieve materials were used as set forth in Table 1 below. In Table 1 the column headed "Type of Molecular Sieve Used" sets forth a tabulation of molecular sieves which are commercially available and each of the adsorbents have a heat of water adsorption are ineffective with respect to providing a process for production of fungible polytetramethylene ether glycol. The empirical chemical formula of the material is set forth in the Table and the percent butyl aldehyde expressed as area percent of the vapor phase chromatograph peak with respect to the area of all the chromatography peaks for that sample is tabulated also. The effective pore size is also listed in Table 1. Only tests 4 and 6 are in accordance with this invention.

Table 1

| Test No. | Type of Molecular Sieves Used | Nominal Pore Diameter in Anstroms | Structure of Molecular Sieves | % Butyl Aldehyde as Area % of an Impurity in THF |
|---|---|---|---|---|
| 1 | None | — | — | 0.016 |
| 2 | 3A | 3 | $K_{12}[(AlO_2)_{12}(SiO_2)_{12}] \cdot XH_2O$ | 0.008 |
| 3 | None | — | — | 0.020 |
| 4 | 4A | 4 | $N_{a12}[(AlO_2)_{12}(SiO_2)_{12}] \cdot XH_2O$ | 0.000 |
| 5 | None | — | — | 0.013 |
| 6 | 5A | 5 | $Ca_{45}Na_3[(AlO_2)_{12}(SiO_2)_{12}] \cdot XH_2O$ | 0.000 |
| 7 | None | — | — | 0.014 |
| 8 | 13X | 10 | $Na_{86}[(AlO_2)86(SiO_2)_{106}] \cdot XH_2O$ | 0.002 |
| 9 | None | — | — | 0.020 |
| 10 | 13X | 10 | $Na_{86}[(AlO_2)_{86}(SiO_2)_{106}] \cdot XH_2O$ | 0.008 |

EXAMPLE 3

The procedure of Example 1 is repeated except that instead of the molecular sieve referred to therein a molecular sieve which is commercially available under the trade signation AW300 (TM Union Carbide) was used. This molecular sieve is reported to have a nominal pore size of 4.0 A and is reportedly chemically modified to provide acid resistance. However, the thermodynamic properties are also altered. The average heat of adsorption for water for the molecular sieve used in this numbered example is about 1,450 btu/-pound $H_2O$.

Thus, this example is not in accordance with the present invention, and is provided for the purpose of illustrating that the pore size alone does not adequately define the present invention. It further illustrates the criticality of the thermodynamic characteristics as indicated by the heat of adsorption of water with respect to the definition of the molecular sieves which are used in accordance with the present invention. The tetrahydrofuran which is untreated and which is used as the tetrahydrofuran in the procedure of this numbered example has 0.016 area percent of butyl aldehyde in the tetrahydrofuran, and after treatment at room temperature in accordance with the procedures of this example the percent of the impurities remained at 0.007 percent on the same basis.

EXAMPLE 4

The purpose of this example is to illustrate the use of the tetrahydrofuran prepared in accordance with the present invention in the manufacture of polytetramethylene ether glycol. The test procedure which was employed in accordance with the present invention and which is referred to hereinafter as the standard test procedure is as follows: 1,550 grams of tetrahydrofuran is placed in a three-neck reactor-container outfitted with a stirrer, thermometer, and a dropping funnel. The dropping funnel is vented through a drying tube. 235 grams of fluosulfonic acid is placed in the dropping funnel and the fluosulfonic acid is introduced into the tetrahydrofuran drop-wise over a period of 15 minutes starting with the temperature of the tetrahydrofuran being approximately 25°C. at the initial introduction of the fluosulfonic acid thereto.

An exotherm is observed during the addition, and the temperature of the reaction is maintained at approximately 35°C. during the addition by external cooling thereof. The temperature is maintained at 35°C. for approximately 1 hour including the 12 mins. addition time, and is thereafter cooled by external cooling to 25°C. 1.5 liters of ion free water is plunged into the reaction mass which is controlled to be maintained at approximately 25°C. The resulting admixture is then steam distilled wherein unreacted tetrahydrofuran is removed. After the removal of tetrahydrofuran is complete the resulting material is permitted to separate into a water and polytetramethylene ether glycol layer and the polytetramethylene ether glycol are separated. The polytetramethylene ether glycol is cooled to below 80°C. and approximately 2 liters of tolulene is added thereto and admixed therewith. Upon admixture additional water separates and the additional water is separated. 20 grams of solid calcium hydroxide and 5 grams of activated carbon (Nuchar CN T. M. West Virginia Pulp & Paper Company) is added thereto. The resulting admixture is thoroughly admixed by agitation and heated to 100°C. during which some additional water is removed by azeotropic distillation and the heating is discontinued when the overhead temperature reaches 110°C.

The tolulene solution of polytetramethylene ether glycol is then filtered through a celite bed and the filtrate is subjected to vacuum distillation at about 15 mm of mercury to remove most of the tolulene, after which it is placed in a high vacuum distillation unit and distilled until 0.02 mm Hg at 95°–100°C. is maintained for about 1 hour. The resulting pot residue is then pressure filtered through another celite bed and the acid number of the resulting product is determined.

When the tetrahydrofuran which is purified in accordance with Example 2 using the 4A molecular sieves the acid number of the resulting polytetramethylene ether glycol is 0.000 mg.KOH/g, whereas when the tetrahydrofuran which was not purified by that procedure and had 0.20 area percent butyl aldehyde was used the acid number of the polytetramethylene ether glycol made therefrom in accordance with the procedure of this example was 0.018 mg.KOH/g.

It has been observed that the acid number of the polytetramethylene ether glycol produced in accordance with this standard procedure generally is approximately the same as the number of the area percent of the suspect trace impurity in the tetrahydrofuran which is thought to be butyl aldehyde. This observation is made only for the purpose of disclosing possible proportionality between these characteristics, and is not intended to be limiting with respect to the performance of the method of this invention.

It should be emphasized that it is not my intention to give undue emphasis to any theories, or to be limited by any theories, but it does appear that an impurity in the tetrahydrofuran which is not removable by the usual standard work-up procedures is effectively removed by the treatment in accordance with the present invention and that upon preparation of polytetramethylene ether glycol from the purified tetrahydrofuran results in a polytetramethylene ether glycol product in which the apparently irreducible acid level is reduced to zero.

Thus, in accordance with the procedure of the present invention, it is now possible for the first time to produce polytetramethylene ether glycol having substantially zero acid numbers and thus polytetramethylene ether glycol prepared from tetrahydrofuran from various sources can be regarded as a fungible commodity, inasmuch as the acid numbers thereof can be reduced to zero using standard commercial procedures.

In the illustrative examples, one standard method for polymerization of tetrahydrofuran and recovery of the polytetramethylene ether glycol is given, and it will be appreciated that the practice of this invention is not limited to particular polymerization or recovery procedures. Given the disclosure herein, those skilled will recognize many variations of specific embodiments within the scope of this invention not only in the contacting of tetrahydrofuran with the defined molecular sieves, but in its polymerization and recovery of polytetramethylene ether glycol.

For example, the exact chemical constitution of the crystalline zeolite constituting the molecular sieve is not critical, except that the required parameters set forth herein must be provided in accordance with this invention.

I claim:

1. In a method for manufacturing polytetramethylene ether glycol in which ingredient tetrahydrofuran is polymerized with a tetrahydrofuran-polymerization catalyst to form a catalytically active tetrahydrofuran-catalyst-polymer mixture, and wherein the catalytic activity of said catalytically active mixture is terminated by the addition of water or 1,4-butene diol thereto, wherein the resulting mixture includes excess tetrahydrofuran and polytetramethylene ether glycol, wherein said resulting mixture is subjected to distillation for removal of said excess tetrahydrofuran therefrom, to contact with solid neutralizing agents, and to mechanical separation steps for removal of water therefrom, the improvement comprising: prior to contacting of said ingredient tetraphydrofuran with the tetrahydrofuran-polymerization catalyst, contacting liquid tetrahydrofuran containing n-butyl aldehyde and having a water content of less than 0.5 percent with a molecular sieve having a nominal pore size in the range 4–5 A inclusive and having a heat of adsorption of about 1,800 btu/pound water ± 100 but/pound of water, continuing said contacting until said n-butyl aldehyde is completely removed from the liquid tetrahydrofuran, separating liquid tetrahydrofuran from the molecular sieve, and using the separated tetrahydrofuran as said tetrahydrofuran ingregient.

2. The method of claim 1 wherein the molecular sieve is the sodium alumino silicate commercially identified as type 4A.

3. The method of claim 1 wherein the molecular sieve is a calcium alumino silicate commercially identified as type 5A.

* * * * *

UNITED STATES PATENT OFFICE
CERTIFICATE OF CORRECTION

PATENT NO. : 3,935,252
DATED : January 27, 1976
INVENTOR(S) : Hideo Tomomatsu

It is certified that error appears in the above-identified patent and that said Letters Patent are hereby corrected as shown below:

On the title page of the patent at entry [21] the Application Number "566,968" should be --506,968--.

Column 3, line 49 "$H_1O$" should read --$H_2O$--.

Claim 1, column 8, line 24 "ingregient" should read --ingredient--.

Signed and Sealed this

Sixth Day of July 1976

[SEAL]

Attest:

RUTH C. MASON
*Attesting Officer*

C. MARSHALL DANN
*Commissioner of Patents and Trademarks*